US011730340B2

(12) United States Patent
Granneman

(10) Patent No.: US 11,730,340 B2
(45) Date of Patent: Aug. 22, 2023

(54) VIDEO DISPLAY SYSTEM HAVING AN ADAPTIVE OVERLAY

(71) Applicant: KARL STORZ Imaging, Inc., Goleta, CA (US)

(72) Inventor: Russell Granneman, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 16/400,255

(22) Filed: May 1, 2019

(65) Prior Publication Data

US 2020/0345204 A1  Nov. 5, 2020

(51) Int. Cl.
*A61B 1/00* (2006.01)
*A61B 1/04* (2006.01)
(Continued)

(52) U.S. Cl.
CPC ........ *A61B 1/00045* (2013.01); *A61B 1/0004* (2022.02); *A61B 1/0005* (2013.01); *A61B 1/000094* (2022.02); *A61B 1/043* (2013.01); *A61B 1/0638* (2013.01); *H04N 5/2628* (2013.01); *H04N 5/272* (2013.01); *H04N 7/183* (2013.01); *H04N 23/56* (2023.01); *H04N 23/555* (2023.01)

(58) Field of Classification Search
CPC ... A61B 1/0005; A61B 1/00039; A61B 1/043; A61B 1/0638; A61B 1/00045; A61B 1/00009; H04N 5/2256; H04N 5/2628; H04N 5/272; H04N 7/183; H04N 2005/2255
See application file for complete search history.

(56) References Cited

U.S. PATENT DOCUMENTS 6,804,549 B2   10/2004  Hayashi
8,229,548 B2    7/2012  Frangioni
(Continued)

FOREIGN PATENT DOCUMENTS

WO      2016/154589 A1    9/2016

OTHER PUBLICATIONS

Mäki-Mantila, M; Extended European Search Report, dated Aug. 28, 2020 pp. 1-7, Munich Germany. Application No. 20171598.4-1122.

(Continued)

*Primary Examiner* — Nasim N Nirjhar
(74) *Attorney, Agent, or Firm* — David N. Villalpando; Honigman LLP

(57) ABSTRACT

The present disclosure is directed towards a video display system and an endoscopic system configured to provide the surgeon with an optimized video image based upon user preference. The video display system includes a first video image displaying a white light video of a surgical site. The first video image has a first predetermined area. A second video image is overlaid on the first video image. The second video image is displayed in a fluorescent light video. The second video image is centered on the surgical site and includes a second predetermined area. The second predetermined area is smaller than the first predetermined area so as to define a boundary of white light video. Thus, the video display system provides the surgeon with the ability to reference the location of the fluorescent light video with respect to anatomical features of the surgical site.

14 Claims, 4 Drawing Sheets

(51) Int. Cl.
*A61B 1/06* (2006.01)
*H04N 5/225* (2006.01)
*H04N 5/262* (2006.01)
*H04N 5/272* (2006.01)
*H04N 7/18* (2006.01)
*H04N 23/56* (2023.01)
*H04N 23/50* (2023.01)

(56) References Cited

U.S. PATENT DOCUMENTS

| | | | |
|---|---|---|---|
| 9,532,719 B2 | 1/2017 | Shida | |
| 9,906,739 B2 | 2/2018 | Sugano | |
| 2003/0191368 A1* | 10/2003 | Wang | G01J 3/4406 |
| | | | 600/160 |
| 2005/0182321 A1* | 8/2005 | Frangioni | A61B 1/00186 |
| | | | 600/431 |
| 2008/0108873 A1* | 5/2008 | Gattani | A61B 1/045 |
| | | | 600/168 |
| 2011/0267444 A1* | 11/2011 | Yamaguchi | A61B 1/00009 |
| | | | 348/65 |
| 2012/0154564 A1* | 6/2012 | Hoffman | H04N 13/366 |
| | | | 348/65 |
| 2012/0197086 A1* | 8/2012 | Morris | A61M 16/044 |
| | | | 600/188 |
| 2012/0287238 A1* | 11/2012 | Onishi | A61B 1/0005 |
| | | | 348/45 |
| 2012/0323072 A1* | 12/2012 | Ishihara | A61B 1/00009 |
| | | | 600/109 |
| 2013/0338438 A1* | 12/2013 | Watanabe | A61B 1/0002 |
| | | | 600/109 |
| 2014/0005484 A1* | 1/2014 | Charles | A61B 50/13 |
| | | | 600/201 |
| 2014/0184790 A1* | 7/2014 | Ishihara | A61B 1/00009 |
| | | | 348/135 |
| 2015/0257737 A1* | 9/2015 | You | A61B 8/463 |
| | | | 600/440 |
| 2015/0276602 A1* | 10/2015 | Ishihara | A61B 1/0638 |
| | | | 250/458.1 |
| 2016/0262602 A1 | 9/2016 | Yu | |
| 2017/0020627 A1* | 1/2017 | Tesar | A61B 90/20 |
| 2017/0186163 A1* | 6/2017 | Kim | H04N 5/2254 |
| 2017/0280029 A1* | 9/2017 | Steiner | A61B 1/0005 |
| 2018/0338802 A1* | 11/2018 | Wade | A61B 1/0005 |
| 2018/0368656 A1* | 12/2018 | Austin | A61B 90/20 |
| 2022/0015616 A1* | 1/2022 | DiCarlo | A61B 1/0638 |

OTHER PUBLICATIONS

Alisha V. Dsouza et al, Review of fluorescence guided surgery systems: identification of key performance capabilities beyond indocyanine green imaging Journal of Biomedical Optics, J. Biomed. Opt. 21(8), 080901 (2016).

Maki-Mantila,M.; EPO Office Action, dated Mar. 3, 2023,pp. 1-6; Munich, Germany.

* cited by examiner

VIDEO DISPLAY SYSTEM HAVING AN ADAPTIVE OVERLAY

TECHNICAL FIELD

The disclosure relates to a video display system and method having a first video image and a second video image overlaid on the first video image to facilitate a surgical procedure.

BACKGROUND

Endoscopes are commonly used to provide access to body cavities while decreasing the invasiveness of a surgical procedure. Certain endoscopes include a video display for displaying the surgical site. It is known to have the video display provide a first video image which displays the surgical site using reflected white light and a second video image which displays the surgical site using emitted fluorescent light, for example when using a fluorescing dye such as indocyanine green ("ICG") with an excitation light such as near-infrared light (NIR).

FIG. 1 shows an embodiment of a video display system. The video display system displays video captured by an endoscope. The endoscope is configured to capture the surgical site in both reflected white light due to white illumination light and emitted fluorescent light due to, for example, NIR excitation light. The fluorescent light is illustratively depicted as fluorescence due to excitation of ICG. The video display system includes a display device, which outputs a video image.

The video image may be partitioned into four displays. The first display, also referenced as the main display as the first display is larger than the other displays, is shown on the right side of the video image depicting an enlarged overlay image. Here, the surgical site is displayed using both reflected white light and emitted fluorescent light that has been colored by image processing, which helps features such as blood flow, tumors, malignant melanoma and the like become more visible. On the left side are three different images. The top image shows a white light image of the surgical site. The middle image shows a grayscale image of the fluorescent light of the surgical site. The grayscale image is due to the fluorescence occurring in a wavelength outside the visible spectrum yet detected as luminance by the image sensor. The middle image may show another image corresponding to a wavelength range outside or inside the visible spectrum as known in procedures involving photodynamic diagnosis (PDD), autofluorescence, fluorescein, and the like. In any of these, the middle image may be pseudo-colored by assigning colors to gray values based on specific criterion. The bottom image shows the overlay image that appears enlarged on the right. The overlay image shows how overlaying the a pseudo-colored fluorescent light image on top of the white light image may highlight areas of ICG concentration but may also obscure anatomical features of the white light image where excess ICG concentration occurs.

The system allows the user to select between one of the three images shown on the main display. As shown, such systems require the surgeon to view any one of the three types of display in the main display. For instance, the user may select the white light video, the grayscale video, or the overlay video. In some instances, it is desirable to view the white light video in the main display and reference the overlay video on one of the partitioned displays, or vice-versa as the overlay video obscures certain anatomical features clearly shown in the white light video.

Accordingly, it remains desirable to have a system that optimizes the camera video images by allowing the surgeon to manipulate the overlay to provide a video image, which is customized to the surgeon's preference.

SUMMARY

A video display system for use in a medical procedure and an endoscopic system is provided. The video display system includes a first video image displaying a white light video of the surgical site. The first video image has a first predetermined area. A second video image is overlaid on top of the first video image. The second video image displays a fluorescent light video, which is centered on the surgical site. The second video image has a second predetermined area, which is smaller than the first predetermined area to define a boundary of white light video, which surrounds the second video image. As such, the surgeon is able to view the surgical site in both a fluorescent light video image and a white light video image wherein the white light video image is able to point out anatomical features so as to allow the surgeon to quickly reference where the fluorescent light video image is with respect to the anatomical features of the surgical site.

In one aspect of the video display system and endoscopic system the boundary is a pixelated line what surrounds an entire periphery of the second video image wherein an input may be provided to adjust the thickness of the boundary.

In another aspect of the disclosure, the size of the second video image may be adjusted to increase or decrease the area of the first video image. In another aspect of the disclosure, the transparency of the second video image may be adjusted.

In another aspect of the disclosure, the video display system may include an image processor configured to detect a tool. In particular, the image processor may be configured to detect a cutting tool, wherein the image processor detects the presence of a cutting tool as the cutting tool enters the video display. In yet another aspect of the disclosure, the video display system may be configured to automatically center the second video image on the tool to move the second display with respect to the movement of the tool within the surgical site.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

DETAILED DESCRIPTION OF PREFERRED EMBODIMENTS

Referring generally to the figures, embodiments of the present disclosure directed towards a video display system and an endoscopic system configured to generate a video image of a surgical site is provided. The video display system includes a first video image displaying a white light video of a surgical site. The first video image has a first predetermined area. A second video image is overlaid on the first video image. The second video image is displayed as a fluorescent light video depicting, for example, ICG fluorescence. The second video image is centered on the surgical site and includes a second predetermined area. The second predetermined area is smaller than the first predetermined area to define a boundary of white light video. Thus, the video display system provides the surgeon with the ability to reference the location of the fluorescent light video with respect to anatomical features of the surgical site.

Figure 1:
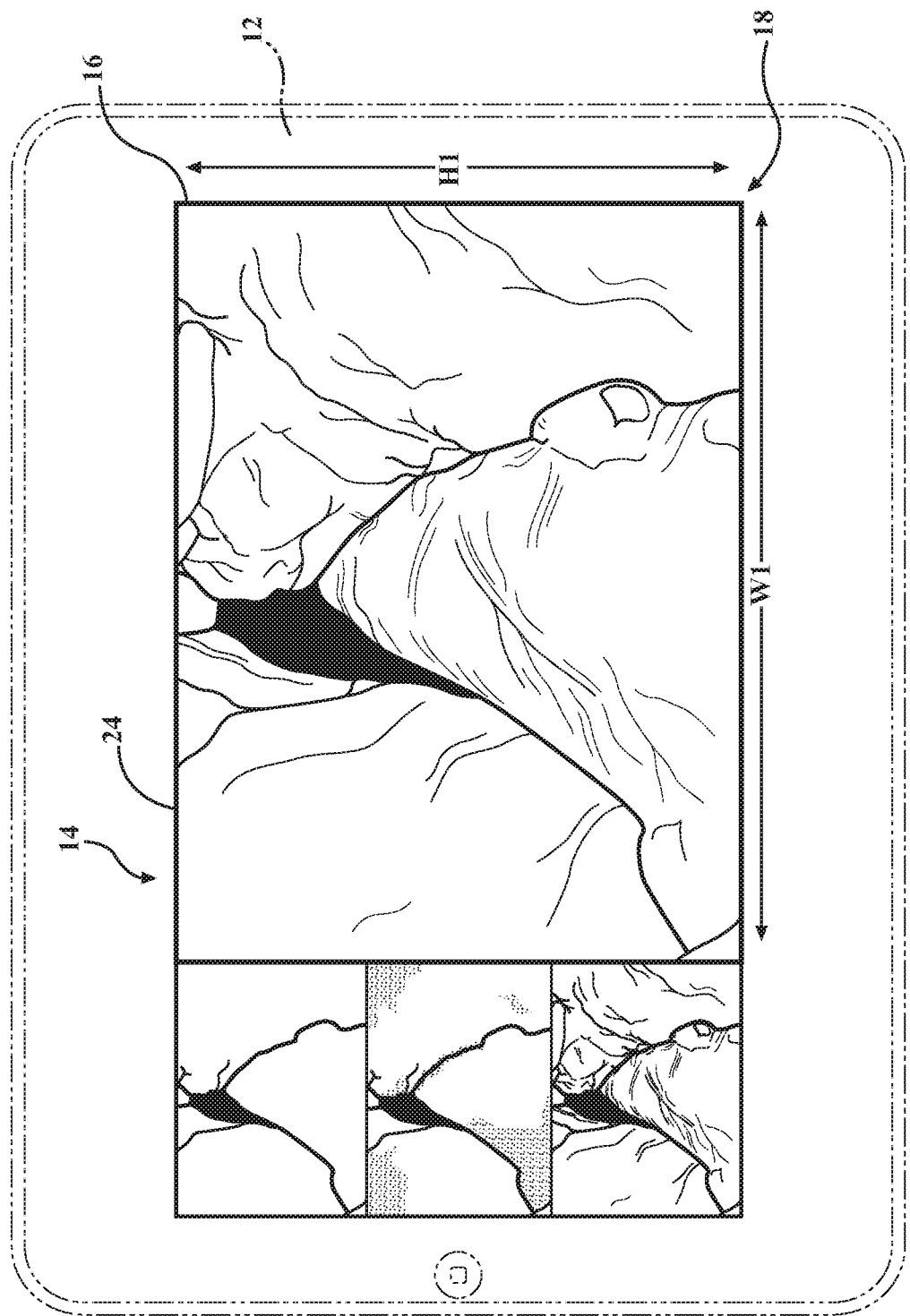
FIG. 1 is a video display system of the prior art.
Figure 2:
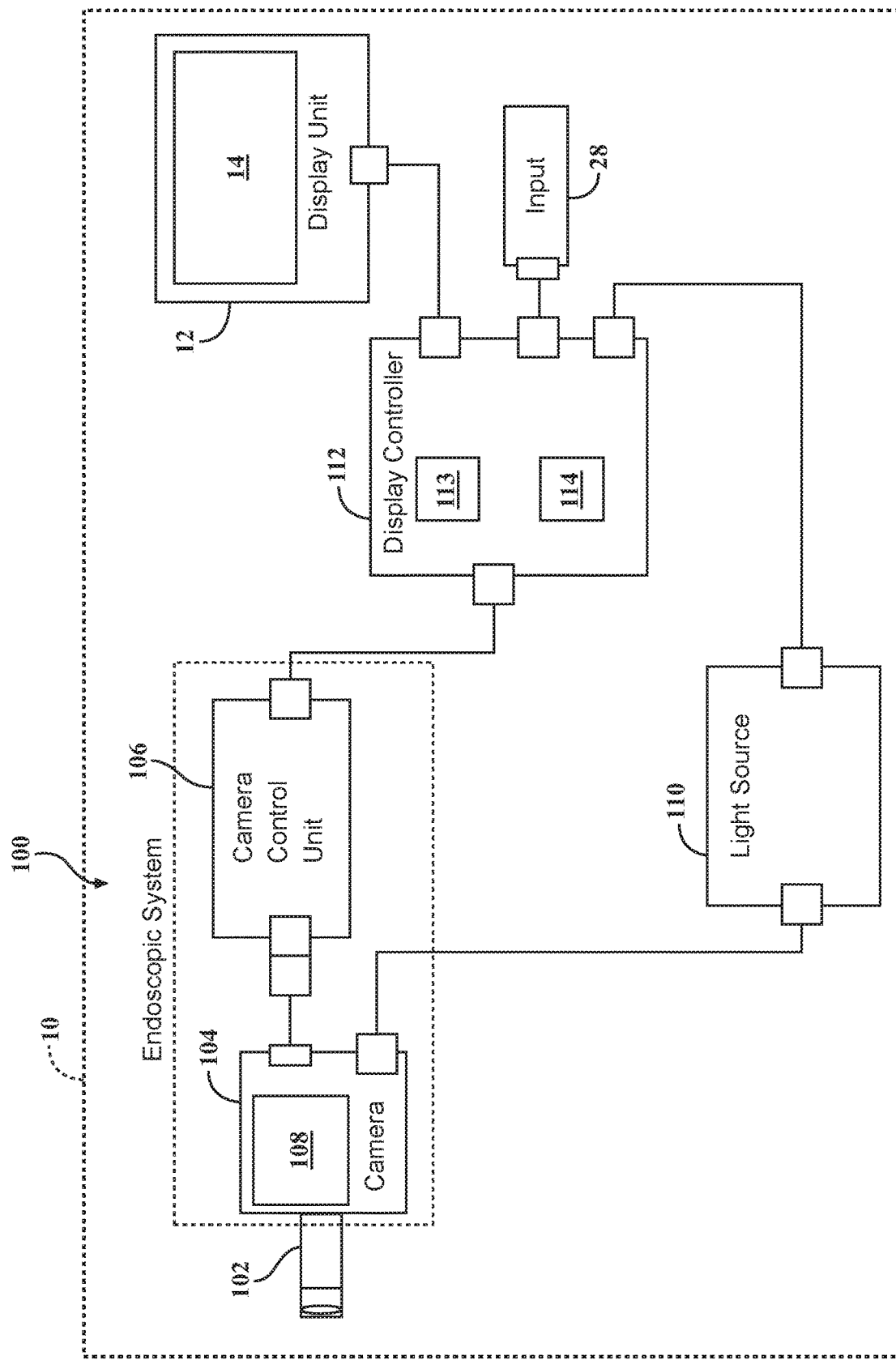
FIG. 2 is a block diagram of an endoscopic system according to one or more embodiments described herein.

With reference first to FIG. 2, the video display system 10 is illustratively shown. For illustrative purposes, a description of video display system 10 is provided within the context of an endoscopic system 100. However, it should be appreciated that the video display system 10 may be utilized in other applications, illustratively including an exoscope, borescopes and other systems having two or more illumination-types and one or more image sensors. Furthermore, although the video display system 10 is described with respect to medical applications using fluorescing dye, it should be understood that industrial applications using other combinations of illumination or excitation light types such as white light, nonvisible light (ultraviolet, infrared, or other), or light within narrow wavelength ranges (visible or nonvisible) may benefit from the same principles.

The endoscopic system 100 includes an endoscope 102 having a camera head unit 104 coupled to the endo scope 102 by optics or optical fiber. The camera head unit 104 is in communication with a camera controller unit 106, through either cable or a wireless connection. The camera control unit 106 controls various processing functions of the camera head unit 104. The camera controller unit 106 may provide a timing signal to the camera head unit 104 to control the actuation of an image sensor 108 and a light source 110 and process the image data from the image sensor 108 to generate a video stream. Alternatively, the light source 110 may generate a timing signal independently of the camera controller unit 106 such that the camera controller unit 106 and the light source 110 operate independently.

The light source 110 is configured to illuminate the surgical site of the endo scope 102 and the image sensor 108 is configured to collect image data from the light source 110. The light source 110 may be formed of one or more light-emitting diodes. The light source 110 may be configured to generate electromagnetic radiation in the visible spectrum commonly called white light and electromagnetic radiation outside the visible spectrum such as near infrared (NIR) excitation light so as to provide for fluorescent imaging such as an indocyanine green (ICG). Other light-emitting diodes may be used to produce various other excitation lights at wavelengths associated with other dyes and auto-fluorescing tissues, proteins, and chemicals of differing procedures.

In some examples, the light source 110 is configured to switch between illuminating with white light and excitation light. The image sensor 108 is actuated to collect image data for both the white light and excitation light sequences. In other examples, the light source 110 is configured to illuminate with white light and excitation light simultaneously. The image sensor 108 is configured to provide an image of the body cavity thereby allowing the surgeon to locate the treatment area and monitor the surgical procedure.

The image sensor 108 can be a complementary metal oxide semiconductor "CMOS" or a charged coupled device "CCD". It should be appreciated that any pixelated image sensor 108 currently known or later developed may be modified and adopted for use herein. In one embodiment, the image sensor 108 is configured to receive electromagnetic radiation in the visible spectrum and in an infrared range between about 800 nanometers to 1200 nanometers associated with a particular field of view. In another aspect, the endoscopic system 100 may include a pair of image sensors 108, wherein one of the image sensors 108 is configured to receive electromagnetic radiation in the visible spectrum with a particular field of view and the other of the image sensors 108 is configured to receive electromagnetic radiation in an infrared range between about 800 nanometers to 1200 nanometers associated with the same particular field of view. One skilled in the art would recognize that various systems using combinations of one or more image sensors 108 may benefit from the principles of the present disclosure.

The video display system 10 includes a display unit 12. The display unit 12 is coupled to the display controller unit 112. Generally speaking, the image sensor 108 delivers image data to the camera controller unit 106, which processes the image data, and outputs processed image data to the display controller unit 112. The display controller unit 112 may arrange videos and images based on the processed image data on the monitor 12 in various ways. In particular, the camera controller unit 106 may provide the image data to the display controller, which includes an image processor 113. The image processor 113 further configures the processed image data collected by the image sensor 108 from both reflected white light and emitted fluorescent light to generate a video image 14, in particular, a white light video image and a fluorescent light video image. As the light source 110 switches between white light and excitation light in synchronization with the exposure and operation of the image sensor 108, the white light and fluorescent light videos are simultaneously displayed to the display unit.

Figure 3:
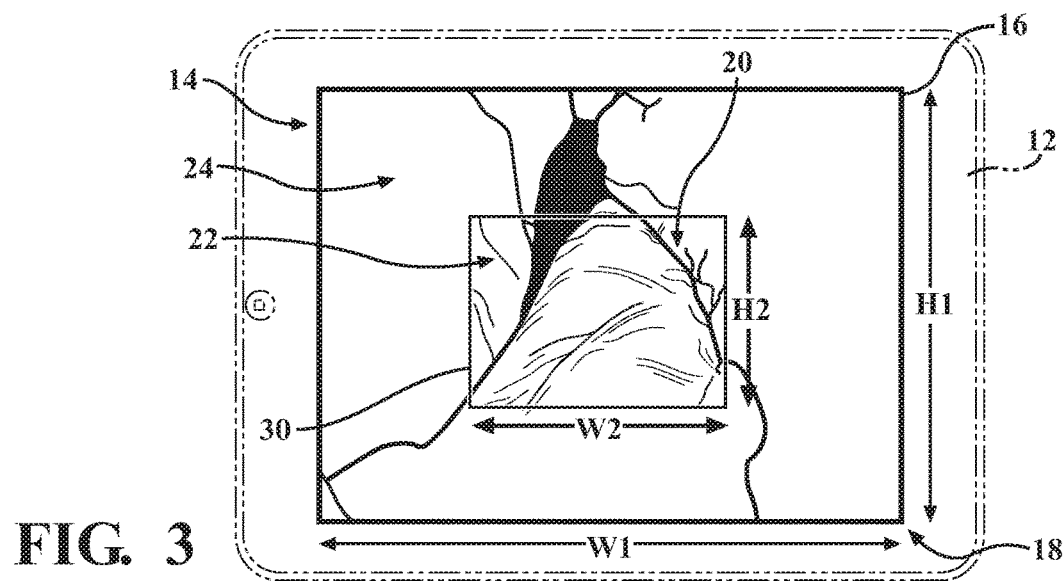
FIG. 3 is a video display showing the first and second video images.

With reference now to FIG. 3, the video image displayed by the display unit 12 is provided. FIG. 3 shows the display unit 12 displaying the video image 14. The video image includes a first video image 16 displaying a white light video having a predetermined field of view of a surgical site, the field of view may be determined by the size of the image sensor 108 and the function of the image processor 113 as is known by those skilled in the art. For instance, the field of view of the image sensor 108 may be purposefully narrowed by digital cropping performed by the image processor 113. The first video image 16 includes a first predetermined area 18, which defines a first width "W1", and a first height "H1" of the video image 14.

The video image 14 further includes a second video image 20. The second video image 20 is overlaid on the first video image 16 wherein the images of the second video image 20 are aligned to the images of the first video image 16. The second video image 20 displays a fluorescent light video, which is centered on the surgical site and aligned with the first video image 16. The second video image 20 has a second predetermined area 22, which defines a second width "W2" and a second height "H2" of the video image 14. The second predetermined area 22 is smaller than the first predetermined area 18 so as to define a boundary 24 of white light video surrounding the second video image 20. Thus, the surgeon can readily identify anatomical features, shown in white light, surrounding the surgical site with respect to the anatomical features such as blood flow, tumors, malignant melanoma and the like which are better shown in fluorescent light video.

For instance, it is known that ICG distribution within the tissue enables intraoperative evaluation of tissue perfusion and vacuolization, identification of critical neurovascular structures and differentiation of tissue plains between lesions and adjacent structures. By maintaining the white light boundary 24 of white light video, critical anatomical features are readily identifiable which ordinarily may be obscured by the overlay of the fluorescent image or require the surgeon to switch to a white light only mode. Such visualization may obscure anatomical features, which are necessary for the surgeon to identify so as to ensure a tool is placed in the proper position. As such, FIG. 3 depicts a video display system 10, which allows the surgeon to manipulate a cutting tool 26 (not shown) within the surgical site and providing anatomical references to help the surgeon place the tool 26 in the proper location.

Figure 4:
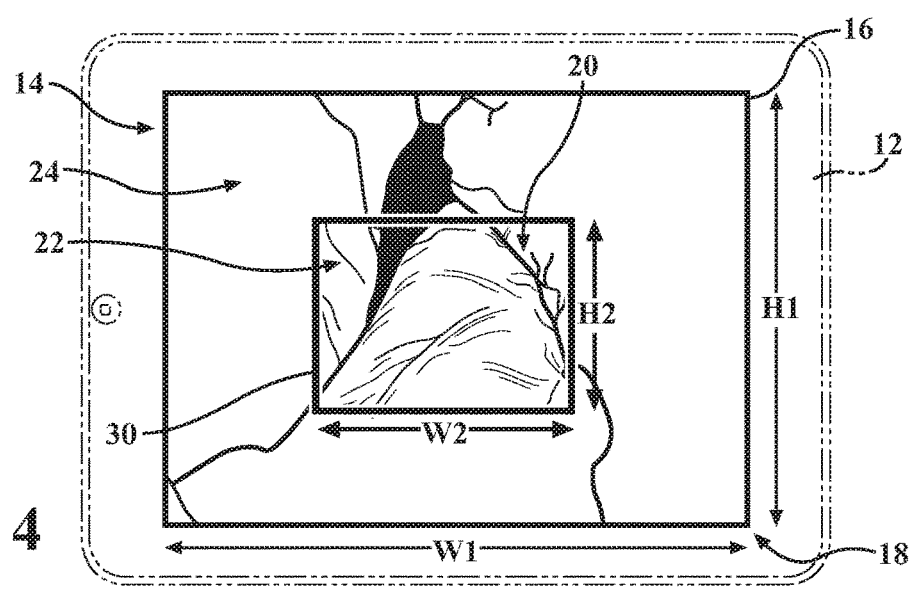
FIG. 4 is an illustrative view of the video display of FIG. 3 showing the thickness of the boundary being modified relative to FIG. 3.

With reference now to FIG. 4 an aspect of the video display system 10 is provided wherein the white light boundary 24 surrounds the peripheral edges of the second video image 20. FIG. 4 depicts an aspect of the video display system 10 wherein an input 28 may be used to differentiate the boundary 24 of white light video from fluorescent light video. FIG. 4 shows the input 28 being configured to increase the thickness of a pixelated boundary, which defines a frame 30.

In particular, the frame 30 delineating the white light boundary 24 from the second video image 20 is thickened relative to what is shown in FIG. 3. The frame 30 is shown in a color different from the pseudo-coloring used with the fluorescent light video shown in the second video image 20. The input 28 may be further configured to adjust the transparency of the frame 30, change a color of the frame 30, or remove the frame 30 in its entirety. Thus, the video image 14 may be optimized to the surgeon's preference to help the surgeon perform the surgical procedure.

Figure 5:
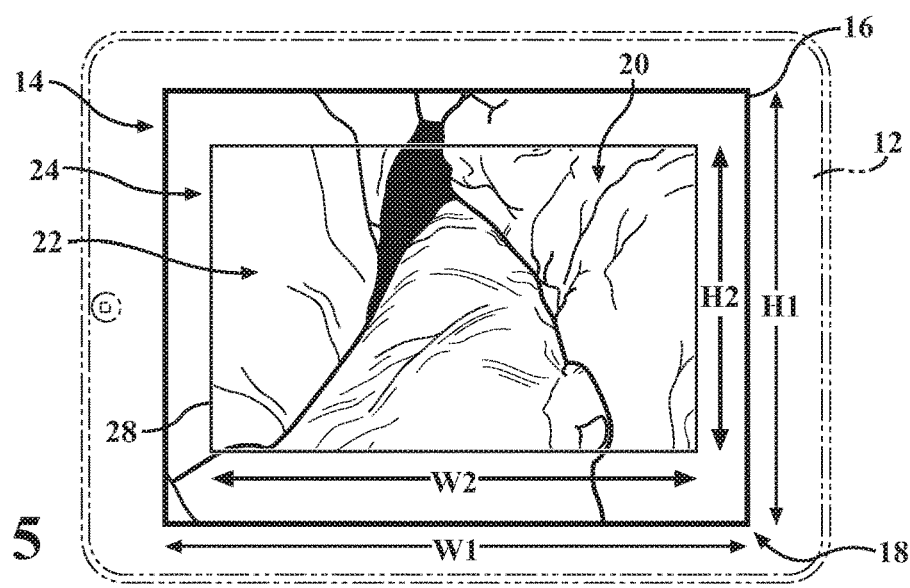
FIG. 5 is an illustrative view of the video display of FIG. 3 showing dimensions of the second video image enlarged relative to FIG. 3.

FIG. 5 depicts another aspect of the video display system 10 wherein the second video image 20 is enlarged with respect to the video image 14 shown in FIGS. 3 and 4. FIG. 5 shows the second video image 20 occupying a greater area relative to the second video image 20 shown in FIG. 3. The adjustment of the second video image 20 may be done by the image processor 113. The size of the second predetermined area 22 may be programmed. The video display system 10 may be configured to adjust the size of the programmed second predetermined area 22 to accommodate the surgeon's preference. The transparency of the second video image 20 may also be adjusted in addition to or irrespective of the size of the second predetermined area 22.

In one aspect, the video display system 10 includes a first image sensor 108*a* and a second image sensor 108*b*. The first image sensor 108*a* has a predetermined pixel array configured to have a predetermined field of view. The first image sensor 108*a* is configured to process white light image. The second image sensor 108*b* has a pixel array of the same dimension as the first image sensor 108*a* and is configured to have the same field of view as the first image sensor 108*a*. The second image sensor 108*b* is configured to gather near infrared image data such as for ICG applications.

In such an embodiment, the image processor 113 crops the image generated by the second image sensor 108*b* so as to produce the second video image 20 which is smaller in size relative to the first video image 16. As the first and second image sensors 108*a*, 108*b* are of the same dimension and have the same field of view, cropping the boundaries of the second video image 20 reduces the size. The image processor 113 then centers the second video image 20 with respect to the first video image 16.

In another embodiment, a single image sensor 108 may be used. In such an embodiment, the size of the second video image 20 is again cropped by the image processor 113. Thus, the input 28 may be configured to provide options for enlarging or decreasing the second video image 20 relative to the first video image 16. As a single image sensor 108 is used in this embodiment, the second video image 20 is always centered with respect to the first video image 16.

In another aspect of the video system, the first image sensor 108*a* is configured to capture white light image data so as to generate the first video image 16 as a white light video. The first image sensor 108*a* may generate the first video image 16 with a first predetermined pixel matrix having a first resolution. The second image sensor 108*b* is configured to capture near infrared image data so as to generate the second video image 20, which is a fluorescent light video. The second image sensor 108*b* has a second predetermined pixel matrix having a second resolution less than the first resolution. The second image sensor 108*b* may be positioned relative to various optical features (prisms, lenses, and beam splitters) such that the second video image 20 captures light at the same focal distance. The first image sensor 108*a* and the second image sensor 108*b* are arranged so as to be centered on the same point, thus the center of each of the first and second video images 16, 20 are the same and can combined with no need for cropping the second video image 20. Accordingly, it should be appreciated that any methods currently known or later developed may be used to produce a second video image 20 of colored light which is smaller than the first video image 16 of white light and the methods and systems described herein are provided for illustrative purposes and are not limiting to the scope of the appended claims.

Figure 6:
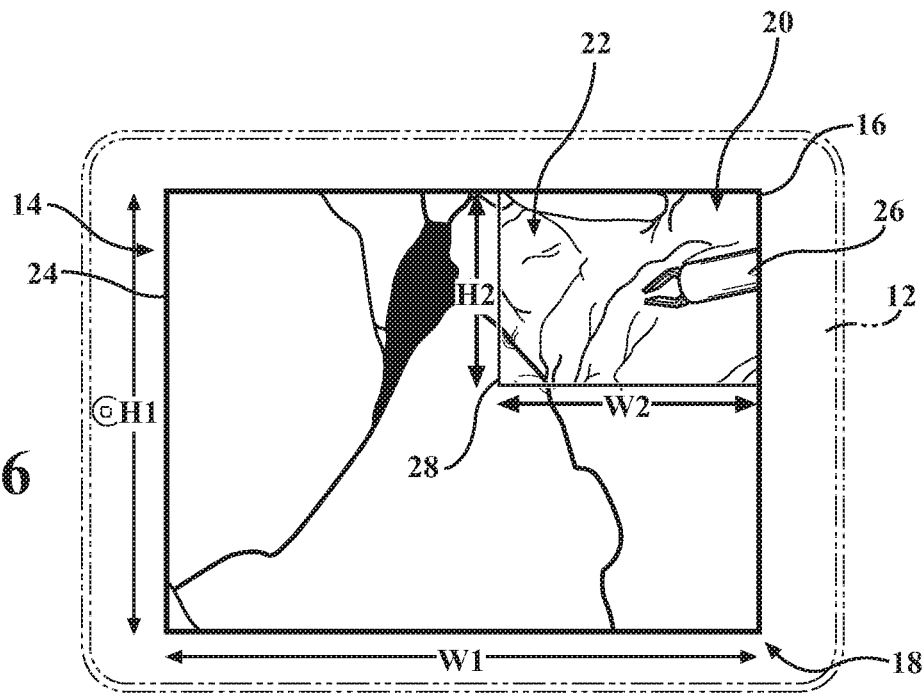
FIG. 6 shows an embodiment of the video display wherein a tool is introduced into the video image.
Figure 7:
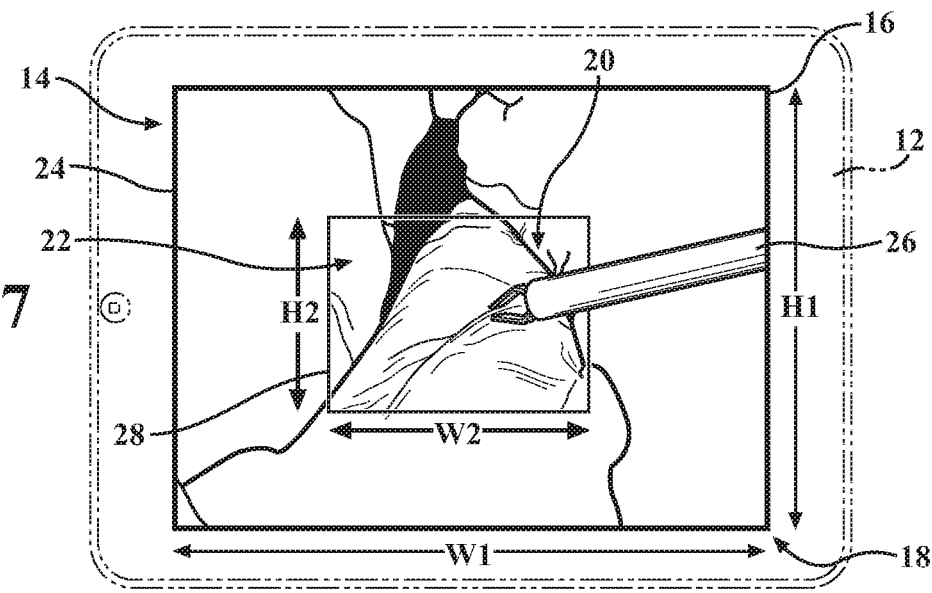
FIG. 7 illustratively depicts the second video image tracking the movement of the tool relative to FIG. 6.

With reference now to FIGS. 6 and 7, an aspect of the video display system 10 is provided wherein the video display system 10 may be configured to move the second video image 20 with respect to a surgical tool 26. For illustrative purposes, the tool 26 is shown as a cutting tool 26 configured to remove tissue. However, it should be appreciated that any other tool used in a surgical procedure may be detected. In such an embodiment, the image processor 113 may be configured to detect the tool 26. The video display system 10 may include a database 114 storing a plurality of different tools 26, wherein through known processes such as edge detection, the image processor 113 may detect the presence of the tool 26 within the video image 14. In such an embodiment, the video display system 10 is configured to move and adjust the video image 14 with respect to the movement of the tool 26 as described in greater detail below.

FIG. 6 shows the tool 26 being introduced into an upper right hand corner of the video image 14. The tool 26 is detected by the image processor 113 and the second video image 20 is moved over to the upper right hand corner of the video image 14 so as to be off-center with respect to the first video image 16. The white light boundary 24 is overshadowed by the second video image 20 with respect to the upper right hand corner of the video display. Alternately, the white light boundary 24 may overshadow the second video image 20 by including a minimum boundary size. Left of the second video image 20 and below the second video image 20, additional portions of the first video image 16 may be revealed. For example, the second video image 20 may be a fixed width "W2" and a fixed height "H2" that shifts with movement of the tool 26. However, a minimum white light boundary 24 may remain, regardless of the movement of the second video image 20. In addition, the white light boundary 24 may increase in areas of the video image 14 further away from the tool 26.

FIG. 7 shows the second video image 20 being moved to the center of the video image 14 in correlation to the movement of the cutting tool 26. It should be appreciated that the second video image 20 may move to other areas within the video image 14 upon movement of the cutting tool 26.

The video display system 10 may include an input 28 which allows for the user to choose one of two modes of operation wherein in a first mode of operation the second video image 20 detects and automatically centers itself around the tool 26 upon the detection of the tool 26 and in a second mode of operation, the second video image 20 remains stationary with respect to the first video image 16 and stays centered with respect to the first video image 16.

In yet another aspect, the second video image 20 may be moved to any location within the field of view of the image sensor 108 so as to provide the surgeon with details regarding tissue perfusion and the like in any area of the field of view of the endoscope 102. Any input 28 currently known or later developed may be modified for use herein, illustratively including a mouse, voice command, eyeglasses, keyboard or the like.

Accordingly, a video display system 10 and an endoscopic system 100 is provided which helps the surgeon conduct a surgical procedure by providing the surgeon with a visible reference of the surgical area. In particular, the video image 14 includes a first video image 16 having a first predetermined area 18 and a second video image 20 overlaid on top of the first video image 16. The second video image 20 has a second predetermined area 22, which is smaller than the first predetermined area 18 so as to form a boundary 24 of white light video image. The boundary 24 of white light video image provides a clearer image of the anatomy of the surgical site relative to the fluorescent light video image of the second video image 20. However, the second video image 20 provides details as to features relating to the treatment of the surgical site such as blood flow, tumors, malignant melanoma and the like. Thus, the video display system 10 and the endoscopic system 100 location of the tool 26 with respect to the treatment site may be easily done by reference to the boundary 24 of the anatomy shown in a white light image.

Further, the video display system 10 and the endoscopic system 100 disclosed herein is customizable based upon the user preference, wherein the dimension of the second video image 20 may be increased or decreased to suit the surgeon's preference. For instance, the second video image 20 may be reduced to show only the area surrounding the surgical area, e.g. around the tool 26, alternatively the second video image 20 may be enlarged so as to cover the entirety of first video image 16. The second video image 20 may also be adjusted to increase or decrease the transparency of the second video image 20. For instance, it may be preferable to reduce the size of the second video image 20 but increase the intensity of the second video image 20 so as to better show features such as blood flow, tumors, malignant melanoma and the like.

Further, the video display system 10 and the endoscopic system 100 disclosed herein may be configured to detect a tool 26. In such an aspect, the second video image 20 is moved to the position of the tool 26. In another aspect, the second video image 20 may be manually moved by the surgeon relative to the first video image 16, such as what is illustratively shown in FIG. 6. Although, FIG. 6 is provided to show the automatic movement of the second video image 20 is response to the detection of a tool 26, it should be appreciated that the teachings of FIG. 6 is not limited to the feature of detecting a tool 26.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A video display system for use in a medical procedure, the video display system a comprising:
   a single camera head unit having an image sensor;
   a light source configured to generate a white light and a fluorescent light;
   a camera controller unit configured to switch the light source between generating white light and fluorescent light and process data from the image sensor so as to generate a white light video stream and a fluorescent light video stream of a surgical site;
   a display controller having an image processor,
   a display monitor for displaying:
   a first video image displaying the white light video of the surgical site having a first predetermined area bounded by a first peripheral edge and taken at a first camera angle;
   a second video image digitally overlaid on the first video image by the image processor, the second video image being the fluorescent light video of a portion of the surgical site, the second video image being digitally cropped by the image processor so as to have a second predetermined area smaller than the first predetermined area and bounded by a second peripheral edge so as to define a boundary of white light video, the boundary defined by a remaining portion of the first video image, wherein the second video image is the same as a portion of the first video image upon which the second video image is overlaid taken by the single camera head at the first camera angle, so as to be aligned with the first video image;
   a frame digitally generated by the image processor, the frame bounding the second peripheral edge of the second video image, the frame being a different color than a pseudo-color applied to the fluorescent light video, wherein the frame and the boundary bounds the second peripheral edge of the second video image so as to provide a reference to anatomical features of the surgical site which may otherwise be obscured by the fluorescent light video;
   an input configured to adjust a size of the second predetermined area, wherein the second video image is digitally cropped by the image processor so as to be a size in response to an actuation of the input; and
   wherein the image processor is further configured to detect a tool and continuously center the second video image on the tool as the tool moves.

2. The video display system as set forth in claim 1, wherein the boundary surrounds an entire periphery of the second video image.

3. The video display system as set forth in claim 1, wherein the input is further configured to adjust a blending of the second video image with the first image.

4. The video display system as set forth in claim 1, wherein the image processor is further configured to detect a tool, wherein the image processor is further configured to center the second video image on the tool.

5. The video display system as set forth in claim 1, further including an input configured to move the second video image with respect to the first video image, wherein the second video image retains the same portion of the first video image upon which the second video image is overlaid during movement.

6. An endoscopic system configured to generate a video image of a surgical site, the endoscopic system comprising:
  a light source configured to transmit electromagnetic radiation in a visible spectrum and in a near infrared spectrum;
  a single camera head unit having an image sensor for acquiring an image data from the light source;
  a display for displaying the video image of the surgical site; and
  an image processor configured to process the image data so as to generate a first video image displaying a white light video of the surgical site taken by the single camera head at a first camera angle, the first video image having a first predetermined area bounded by a first peripheral edge and being displayed on the display, and a second video image digitally overlaid on the first video image, the second video image displaying a fluorescent light video of a portion of the surgical site, the image processor further configured to digitally crop the second video image so as to have a second predetermined area smaller than the first predetermined area and bounded by a second peripheral edge so as to define a boundary of white light video, the boundary defined by a remaining portion of the first video image, wherein the second video image is the same as a portion of the first video image upon which the second video image is overlaid taken at the first camera angle;
  a frame digitally generated by the image processor, the frame bounding the second peripheral edge of the second video image, the frame being a different color than a pseudo-color applied to the fluorescent light video, wherein the frame and the boundary bounds the second peripheral edge of the second video image so as to provide a reference to anatomical features of the surgical site which may otherwise be obscured by the fluorescent light video;
  an input configured to adjust a size of the second predetermined area, wherein the second video image is digitally cropped by the image processor so as to be a size in response to an actuation of the input; and
  wherein the image processor is further configured to detect a tool and continuously center the second video image on the tool as the tool moves.

7. The endoscopic system as set forth in claim 6, wherein the imager is a first imager and a second imager, the first imager configured to capture image data in the visible spectrum and the second imager configured to capture image data in the near infrared spectrum.

8. The endoscopic system as set forth in claim 7, wherein a field of view of the second imager is smaller than a field of view of the first imager.

9. The endoscopic system as set forth in claim 7, wherein a field of view of the first imager is the same as the field of view of the second imager, wherein the image processor crops the second video image.

10. The endoscopic system as set forth in claim 7, wherein the first imager has a larger pixel array than the second imager.

11. The endoscopic system as set forth in claim 6, wherein the boundary surrounds an entire periphery of the second video image.

12. The endoscopic system as set forth in claim 6, wherein the input is further configured to adjust a transparency of the second video image.

13. The endoscopic system as set forth in claim 6, wherein the image processor is further configured to detect a tool, wherein the image processor is further configured to center the second video image on the tool.

14. The endoscopic system as set forth in claim 6, further including an input configured to move the second video image with respect to the first video image, wherein the second video image retains the same portion of the first video image upon which the second video image is overlaid during movement.

* * * * *